US009568408B2

United States Patent
Jamison

(10) Patent No.: US 9,568,408 B2
(45) Date of Patent: Feb. 14, 2017

(54) METHODS FOR DETERMINING RHEOLOGICAL QUANTITIES OF A DRILLING FLUID USING APPARENT VISCOSITY

(71) Applicant: Halliburton Energy Services, Inc., Houston, TX (US)

(72) Inventor: Dale E. Jamison, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/889,122

(22) PCT Filed: Dec. 19, 2014

(86) PCT No.: PCT/US2014/071381
§ 371 (c)(1),
(2) Date: Nov. 4, 2015

(87) PCT Pub. No.: WO2016/099536
PCT Pub. Date: Jun. 23, 2016

(65) Prior Publication Data
US 2016/0341646 A1 Nov. 24, 2016

(51) Int. Cl.
*E21B 49/08* (2006.01)
*E21B 21/08* (2006.01)
(Continued)

(52) U.S. Cl.
CPC ............... *G01N 11/14* (2013.01); *E21B 7/00* (2013.01); *E21B 21/08* (2013.01); *E21B 47/00* (2013.01);
(Continued)

(58) Field of Classification Search
CPC .... E21B 49/08; E21B 21/08; E21B 2049/085; G01N 11/14
See application file for complete search history.

(56) References Cited

U.S. PATENT DOCUMENTS

2013/0146357 A1 6/2013 Lovorn
2014/0046628 A1 2/2014 Ligneul et al.
(Continued)

FOREIGN PATENT DOCUMENTS

CN 102839934 A 12/2012
EP 0123608 A1 10/1984
(Continued)

OTHER PUBLICATIONS

International Search Report and Written Opinion for PCT/US2014/071381 dated Aug. 21, 2015.
(Continued)

*Primary Examiner* — Giovanna C Wright
(74) *Attorney, Agent, or Firm* — McDermott Will & Emery LLP; Tenley Krueger

(57) ABSTRACT

Rheological quantities, such as shear stress, can sometimes be difficult to determine under extreme temperature and pressure conditions. In contrast, the relative rheology of a fluid can often be readily determined over a range of temperature and pressure conditions. The relative rheology can then be used to scale a rheological quantity of the fluid to a given temperature and pressure condition. Methods for scaling a rheological quantity can comprise: measuring an apparent viscosity of a drilling fluid at first, second and third reference temperature and pressure conditions; determining a rate of change in apparent viscosity with respect to temperature at a substantially equal pressure; determining a rate of change in apparent viscosity with respect to pressure at a substantially equal temperature; and scaling a rheological quantity from an initial set of temperature and pressure conditions to a final set of temperature and pressure conditions using the rates of change.

22 Claims, 2 Drawing Sheets

(51) Int. Cl.
    *G01N 11/14*    (2006.01)
    *E21B 47/00*    (2012.01)
    *E21B 7/00*     (2006.01)
    *E21B 47/06*    (2012.01)

(52) U.S. Cl.
    CPC ............ *E21B 47/06* (2013.01); *E21B 47/065* (2013.01); *E21B 49/08* (2013.01); *E21B 2049/085* (2013.01)

(56) References Cited

U.S. PATENT DOCUMENTS

| | | |
|---|---|---|
| 2014/0262516 A1 | 9/2014 | Larson |
| 2014/0333754 A1 | 11/2014 | Graves et al. |
| 2015/0020588 A1 | 1/2015 | Larson |

FOREIGN PATENT DOCUMENTS

| | | |
|---|---|---|
| EP | 0211112 A1 | 2/1987 |
| EP | 2045594 A1 | 4/2009 |
| EP | 2911188 A1 | 8/2015 |
| WO | 0102832 A1 | 1/2001 |
| WO | 2010/116228 A2 | 10/2010 |
| WO | 2015/002653 A1 | 1/2015 |
| WO | 2016099536 A1 | 6/2016 |

OTHER PUBLICATIONS

Search Report received in corresponding Application NL1041678, dated Nov. 9, 2016.

METHODS FOR DETERMINING RHEOLOGICAL QUANTITIES OF A DRILLING FLUID USING APPARENT VISCOSITY

CROSS-REFERENCE TO RELATED APPLICATIONS

This application is a 35 U.S.C. §371 national stage application of International Patent Application PCT/US2014/071381.

BACKGROUND

The present disclosure generally relates to rheological properties, and, more specifically, to methods for determining the rheology of drilling fluids in a wellbore.

Drilling fluids, also known as drilling muds, are specially designed treatment fluids that are circulated through a wellbore to facilitate a drilling operation. As used herein, the terms "treat," "treatment," "treating," and grammatical equivalents thereof refer to any subterranean operation that uses a fluid in conjunction with achieving a desired function and/or for a desired purpose. Use of these terms does not imply any particular action by the treatment fluid or a component thereof, unless otherwise specified herein. Drilling fluids can be oil-based or water-based, and the choice of a particular type of drilling fluid may be influenced by various factors. Functions of a drilling fluid during a drilling operation can include, for example, removing drill cuttings from the wellbore, cooling and lubricating the drill bit, aiding in the support of the drill pipe and the drill bit, and maintaining sufficient wellbore pressure to provide wellbore integrity and to prevent blowouts from occurring.

Although the hydrostatic pressure provided by drilling fluids is desirable to stabilize the subterranean formation and to contain fluids in the wellbore, formation damage and fluid loss can result if the wellbore pressure is excessive. Correspondingly, if the wellbore pressure is too low, formation fluids may enter the wellbore and create a blow out situation. Accordingly, it can be desirable to know the equivalent circulating density (ECD) of a drilling fluid in a wellbore in order to help maintain the wellbore pressure in a desired range. ECD represents the combined effect of hydrostatic fluid pressure, hydraulic pressure losses and choke pressure, among other factors. Hydraulic models can be used to predict the ECD and manage wellbore pressures during a drilling process. By applying hydraulic models, a well operator can better regulate and optimize a drilling operation by effectively managing wellbore pressures and maximizing the rate of penetration of the drill bit into the subterranean formation. Such modeling results can be compared to pressure-while-drilling (PWD) measurements in order to actively manage a drilling process by regulating factors such as, for example, pump rates, drill bit rotation rates, rates of penetration, choke pressures, and tripping speeds, not to mention varying the composition of the drilling fluid itself. In the absence of direct pressure measurements, such as PWD, reliance on hydraulic models may be especially important.

The rheology of a drilling fluid can determine whether it is able to deliver sufficient cuttings transport and sag resistance while maintaining pressure in a wellbore under a particular set of temperature and pressure conditions. Effects of inadequate rheological properties in a drilling fluid can include, for example, pressure loss in the wellbore, blowouts, weighting agent sag, poor cuttings transport, stuck pipe and the like. Excessive hydrostatic pressures resulting from inadequate rheological properties can also lead to issues such as lost circulation and unintentional fracturing.

Temperature and pressure can significantly impact the rheology of a drilling fluid. Although a drilling fluid may have an initial rheological performance resulting from its formulated composition, the rheological performance can change due to added materials (e.g., drill cuttings) entering the drilling fluid in-process during a drilling operation. The continual influx of drill cuttings and other added materials to a drilling fluid during a drilling operation in a wellbore can significantly complicate the determination of the drilling fluid's rheological performance. Drill cuttings and other added materials from the wellbore may be highly variable in nature, and the amount and identity of added materials present in the drilling fluid at any given point in time can fluctuate. Such variability can make it difficult to determine true composition of a drilling fluid and its associated rheological properties at any given time or wellbore locale, particularly when considering the further factors of temperature and pressure variance within the wellbore. Accordingly, it is often difficult to accurately model the downhole rheological performance of a drilling fluid based only upon measurements obtained in a laboratory setting.

Certain rheological properties, such as a fluid's change in apparent viscosity as a function of temperature and/or pressure, may be readily measured over a wide range of temperature and pressure conditions. However, some rheological properties can be difficult to determine under extreme temperature and pressure conditions, even in a laboratory setting, due to instrumental limitations. For example, shear stress and shear rate are rheological quantities that may be especially useful in determining a drilling fluid's ECD in a wellbore, but they can be difficult to measure under extreme temperature and pressure conditions. Although shear stress and shear rate may be readily measured in a laboratory setting at routine temperatures and pressures using a couette-style viscometer (e.g., a Fann 35 viscometer), many couette-style viscometers are completely unsuitable for use in the extreme temperatures and pressures that are commonly encountered downhole. Those that are adaptable to extreme temperature and pressure conditions (e.g., Fann 75 and Fann 77 viscometers) are exceedingly cumbersome and time-consuming to use. Accordingly, there is presently no simple way to determine certain high-interest rheological quantities of a drilling fluid under the temperature, pressure and compositional in-process conditions present within a wellbore. Other factors that may be of note in determining such rheological quantities in a wellbore environment include the variable and transient temperatures of a fluid progressing through the wellbore due to heat transfer to and from the subterranean formation, and extreme swings in temperature range, such as those encountered in deepwater drilling operations.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

Figure 1:
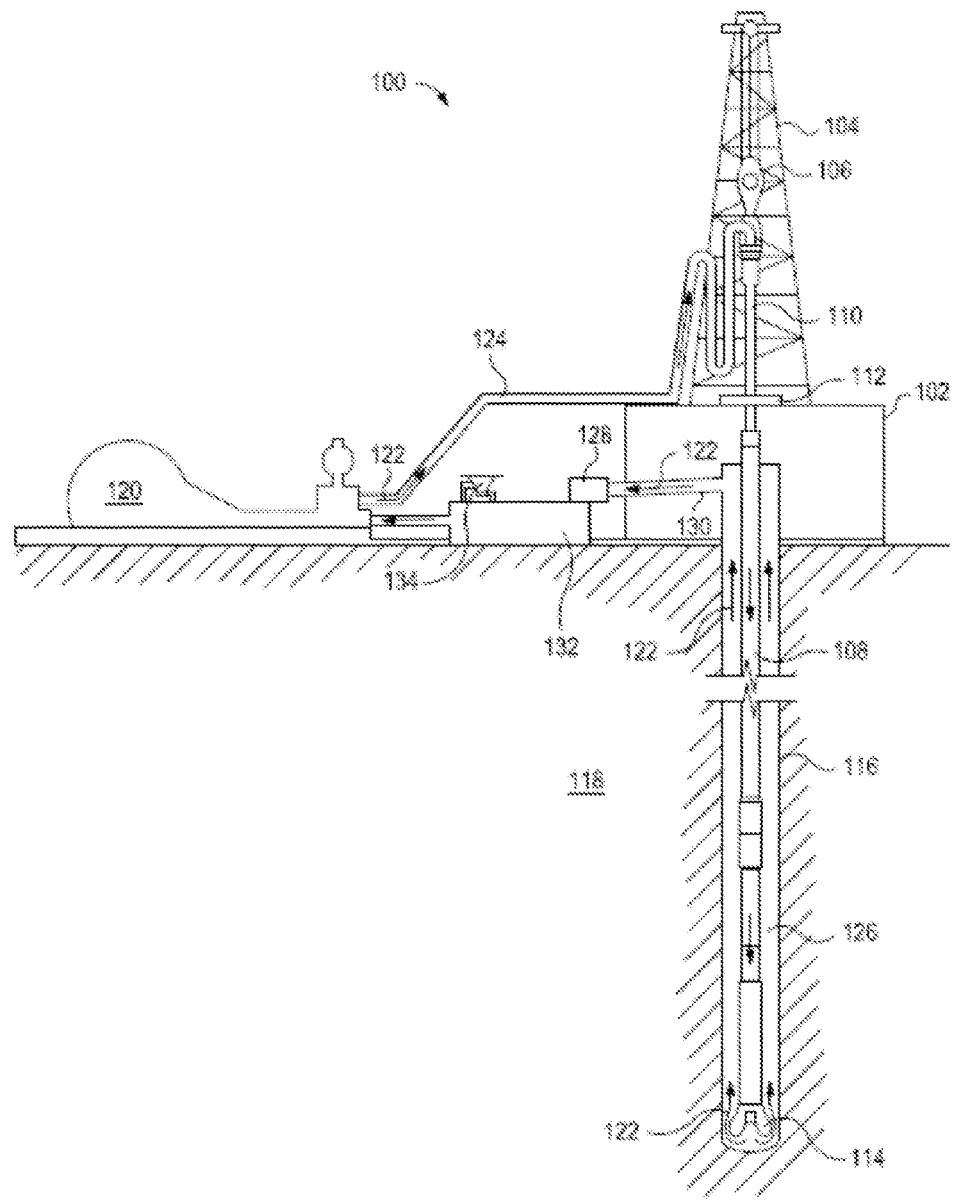
FIG. 1 shows an illustrative schematic of a wellbore drilling assembly.

The present disclosure generally relates to rheological properties, and, more specifically, to methods for determining the rheology of drilling fluids in a wellbore.

One or more illustrative embodiments incorporating the features of the present disclosure are presented herein. Not all features of a physical implementation are necessarily described or shown in this application for the sake of clarity. It is to be understood that in the development of a physical implementation incorporating the embodiments of the present disclosure, numerous implementation-specific decisions may be made to achieve the developer's goals, such as compliance with system-related, business-related, government-related and other constraints, which may vary by implementation and from time to time. While a developer's efforts might be time-consuming, such efforts would be, nevertheless, a routine undertaking for one having ordinary skill in the art and the benefit of this disclosure.

As discussed above, it is presently difficult to measure certain rheological quantities under extreme temperature and pressure conditions, at least without using cumbersome and time-consuming measurement techniques. For example, there is currently no effective way to directly determine shear stress and shear rate of a drilling fluid under the in-process temperature, pressure and compositional conditions present within a particular wellbore environment, at least with a reasonably rapid analysis time.

Unlike many couette-style viscometers, other types of viscometers are relatively amenable toward use under the extreme temperature and pressure conditions that are commonly encountered in a wellbore environment. A number of viscometers, such as vibrational viscometers, for example, are rugged and have no moving parts, making them well suited for use in harsh, in-process environments, including within a wellbore. Vibrational viscometers also provide a rapid data output, thereby giving them the potential to provide an element of real-time or near real-time process feedback. A disadvantage of vibrational viscometers and many other types of rugged viscometers in comparison to couette-style viscometers, however, is that they can only provide a relative measure of rheology, rather than returning a shear rate or a shear stress, such as can be provided when using a couette-style viscometer.

The present inventor recognized that the relative measure of rheology provided by a rugged viscometer, such as a vibrational viscometer, can be used to scale the rheological data (i.e., shear rate or shear stress) obtained from a couette-style or like style viscometer from one set of temperature and pressure conditions to another. This discovery can be particularly advantageous in situations where the rheological quantity is to be scaled to a set of temperature and pressure conditions where the rheological performance is not readily measurable using a couette-style viscometer. Specifically, the inventor recognized that the apparent viscosity provided by a vibrational viscometer or similar viscometer may be used to scale the shear rate and shear stress data provided by a couette-style viscometer to any set of temperature and pressure conditions within a defined calibration range. That is, the inventor recognized that the apparent viscosity of a fluid is related to its other rheological properties, such as the shear stress and shear rate, which may be of higher interest for fluid modelling purposes. For example, the apparent viscosity of a drilling fluid under standard temperature and pressure conditions may be used to calculate a rheological quantity of the drilling fluid at a temperature and pressure where the rheological performance is unknown, thereby allowing an estimated value of the equivalent circulating density to be determined. As used herein, the term "apparent viscosity" refers to the viscosity of a fluid measured at a given shear rate at a fixed temperature and pressure. Other rheological quantities may be scaled in a like manner with a rapid response time. For example, gel strengths may also be scaled similarly using the processes of the present disclosure to obtain the gel strength at a particular set of temperature and pressure conditions. Knowing the gel strength can be desirable for determining pump start up pressures and tripping speeds during a drilling operation.

Although several types of viscometers may be used to determine the apparent viscosity of a drilling fluid, vibrational viscometers may be especially well suited for measurements made at the extreme temperature and pressure conditions found in a wellbore, since they often employ no dynamic seals or rotational parts. Illustrative vibrational viscometers, such as those supplied by Sofraser, Inc., utilize a magnetically actuated rod that extends into a test fluid and is supported by a flexure seal. The vibrational response of the rod upon actuation, typically measured at its resonant frequency, is related to the viscosity of the test fluid, and an output of the vibrational viscometer may be correlated to the apparent viscosity of the test fluid.

The apparent viscosity may then be used to scale shear stress and shear rate rheological data between temperature and pressure conditions residing within a defined calibration range, as described in more detail herein. Due to the rapid output provided by a vibrational viscometer, the calculated values of the shear stress and shear rate may be determined much more rapidly than by directly measuring these quantities using other measurement techniques. The scaling may occur essentially in real-time or near real-time, thereby providing the potential for realizing proactive or reactive control of a drilling process. For example, calculated values of the shear rate and shear stress may be used to determine the equivalent circulating density of a drilling fluid under a particular set of in-process conditions within a wellbore. By monitoring the equivalent circulating density and pressure-while-drilling during a drilling operation, the drilling operation may be regulated to respond to the particular in-process temperature, pressure or compositional conditions present in the wellbore. As a measure of quality control, predicted wellbore pressures based on the ECD may be compared to those obtained through PWD.

The methods described herein make use of the rate of change in the apparent viscosity with respect to temperature and with respect to pressure. These rates of change may then be used to scale any rheological quantity to a particular set of temperature and pressure conditions that are within a defined calibration range. As an initial estimate, it may be presumed that the rates of change are constant over the calibration range (i.e., that the rheological property varies linearly with temperature and pressure). If a more accurate determination of the calculated rheological quantity is needed, particularly if the rate of change with respect to temperature and/or pressure varies significantly from linearity, a calibration function can be obtained over a plurality of temperature and pressure conditions. By consulting the calibration function(s), the actual rate of change in the apparent viscosity with respect to temperature or pressure may be obtained from a plot of the calibration function. Either approach is encompassed by the embodiments described herein.

In some embodiments, the methods described herein may comprise obtaining an apparent viscosity of a fluid using a rugged viscometer under an initial set of temperature and pressure conditions and using this value to scale the apparent viscosity or another rheological quantity to a final set of temperature and pressure conditions. This process advantageously avoids having to conduct viscosity measurements on the fluid at the final set of temperature and pressure conditions. Accordingly, the methods described herein may be used to estimate the value of any rheological quantity at the final set of temperature and pressure conditions based upon the apparent viscosity at the initial set of temperature and pressure conditions and its rate of change with respect to temperature and pressure.

In more particular embodiments, the methods described herein may be used to scale a rheological quantity of a drilling fluid to the final set of temperature and pressure conditions, which may be representative of those encountered while the drilling fluid is disposed within a wellbore. The calculated rheological quantity may then be used to provide an estimate of the drilling fluid's downhole rheological performance. Since many types of viscometers can produce a rapid output of absolute viscosity data, proactive control of a drilling operation may be realized in various aspects of the present disclosure. For example, if a real-time or near real-time measurement of the drilling fluid indicates an insufficient equivalent circulating density, various parameters of the drilling operation may be adjusted in order to compensate. Drilling parameters that may be adjusted include, but are not limited to, the drilling fluid composition, the pump rate, the rate of penetration, the drill bit rotation rate, tripping speeds, any combination thereof, and the like.

In some embodiments, methods described herein may comprise: measuring an apparent viscosity of a drilling fluid at a first set of reference conditions comprising a first reference temperature and a first reference pressure, at a second set of reference conditions comprising a second reference temperature and a second reference pressure, and at a third set of reference conditions comprising a third reference temperature and a third reference pressure; wherein at least two of the reference temperatures are substantially equal to one another and at least two of the reference pressures are substantially equal to one another, the reference temperatures and the reference pressures defining a calibration range; determining a rate of change in apparent viscosity with respect to temperature between two of the sets of reference conditions in which the reference pressures are substantially equal; determining a rate of change in apparent viscosity with respect to pressure between two of the sets of reference conditions in which the reference temperatures are substantially equal; and scaling a rheological quantity measured at an initial set of temperature and pressure conditions within the calibration range to a final set of temperature and pressure conditions within the calibration range, the scaling being calculated based upon the rate of change in apparent viscosity with respect to temperature and the rate of change in apparent viscosity with respect to pressure, thereby determining a calculated rheological quantity. In some embodiments, at least some of the measurements to determine the drilling fluid's apparent viscosity can take place while the drilling fluid is disposed in a subterranean formation. In some or other embodiments, the drilling fluid's apparent viscosity may be made under reference conditions that simulate the temperature and pressure conditions found in a given location of the subterranean formation.

In some or other embodiments, methods described herein may comprise: introducing a drilling fluid into a wellbore during a drilling operation; measuring an apparent viscosity of the drilling fluid at a first set of reference conditions comprising a first reference temperature and a first reference pressure, at a second set of reference conditions comprising a second reference temperature and a second reference pressure, and at a third set of reference conditions comprising a third reference temperature and a third reference pressure; wherein at least two of the reference temperatures are substantially equal to one another and at least two of the reference pressures are substantially equal to one another, the reference temperatures and the reference pressures defining a calibration range; determining a rate of change in apparent viscosity with respect to temperature between two of the sets of reference conditions in which the reference pressures are substantially equal; determining a rate of change in apparent viscosity with respect to pressure between two of the sets of reference conditions in which the reference temperatures are substantially equal; scaling a rheological quantity measured at an initial set of temperature and pressure conditions within the calibration range to a final set of temperature and pressure conditions within the calibration range, the scaling being calculated based upon the rate of change in apparent viscosity with respect to temperature and the rate of change in apparent viscosity with respect to pressure, thereby determining a calculated rheological quantity; and regulating the drilling operation in response to the calculated rheological quantity of the drilling fluid or a quantity derived therefrom.

As used herein, a reference temperature or a reference pressure will be considered to be "substantially equal" if the apparent viscosity does not change significantly over the temperature or pressure variance. Typically, for a first temperature or pressure to be considered substantially equal to a second temperature or pressure, the variance in the apparent viscosity between the two temperatures or pressures is less than about 5%. Hence, when measuring the apparent viscosity at each reference condition, some degree of variance can be tolerated in the parameter nominally being held constant.

According to the embodiments described herein, scaling of the rheological quantity may utilize a linear combination of the temperature contribution to the rheological quantity and the pressure contribution to the rheological quantity. In such embodiments, scaling of the rheological quantity may comprise solving Equation 1 for the rheological quantity at a given set of temperature and pressure conditions.

$$Q_F = Q_I + Q_I[(dU/dT)(T_F - T_I) + (dU/dP)(P_F - P_I)] \quad \text{(Equation 1)}$$

In Equation 1, the variables represent the following:
$Q_F$ is the calculated rheological quantity at the final set of temperature and pressure conditions;
$Q_I$ is a measured value of the rheological quantity at the initial set of temperature and pressure conditions;
$dU/dT$ is the rate of change in apparent viscosity with respect to temperature;
$dU/dP$ is the rate of change in apparent viscosity with respect to pressure;
$T_F$ is the temperature at the final set of temperature and pressure conditions;
$T_I$ is the temperature at the initial set of temperature and pressure conditions;

$P_F$ is the pressure at the final set of temperature and pressure conditions; and $P_I$ is the pressure at the initial set of temperature and pressure conditions.

Further explanation regarding the variables and calculation of the rheological quantity at the final set of temperature and pressure conditions follows herein.

In practicing the methods described herein, the apparent viscosity of the drilling fluid is first measured at least at three sets of reference conditions, each comprising a reference temperature and a reference pressure. The reference temperatures and the reference pressures are chosen to define a calibration range within which a rheological quantity may be scaled. That is, the reference conditions establish low and high temperature and pressure values, which define a calibration range for temperature and a calibration range for pressure. Among the three sets of reference conditions, the temperature is held substantially equal in two of the sets of reference conditions, and the pressure is held substantially constant in two of the sets of reference conditions. Such a three-condition measurement allows the linear rate of change in the apparent viscosity with respect to temperature at constant pressure and the linear rate of change in the apparent viscosity with respect to pressure at constant temperature to be determined.

The rate of change in apparent viscosity with respect to temperature and the rate of change in apparent viscosity with respect to pressure is then determined within the calibration range. The rate of change in apparent viscosity with respect to temperature (dU/dT) may be determined by comparing the reference conditions having substantially equal pressures. Specifically, dU/dT may be calculated from Equation 2, wherein $U_1$ and $U_2$ are the apparent viscosity values at two sets of reference conditions having substantially equal pressures and $T_1$ and $T_2$ are the temperatures at two sets of reference conditions having substantially equal pressures.

$$dU/dT=(U_2-U_1)/(T_2-T_1) \quad \text{(Equation 2)}$$

Similarly, the rate of change in apparent viscosity with respect to pressure (dU/dP) may be determined by comparing the reference conditions having substantially equal temperatures. Specifically, dU/dP may be calculated from Equation 3, wherein $U_{1'}$ and $U_{2'}$ are the apparent viscosity values at two sets of reference conditions having substantially equal temperatures and $P_1$ and $P_2$ are the pressures at two sets of reference conditions having substantially equal temperatures.

$$dU/dP=(U_{2'}-U_{1'})/(P_2-P_1) \quad \text{(Equation 3)}$$

There is one apparent viscosity value in common between $U_1$, $U_2$, $U_{1'}$, and $U_{2'}$.

Once dU/dT and dU/dP have been determined, Equation 1 may then be applied to scale any rheological quantity, such as shear rate or shear stress, to particular temperature and pressure conditions within the calibration range without having to actually measure the rheological quantity under those conditions. Specifically, dU/dT and dU/dP may be used to scale a rheological quantity measured at an initial set of temperature and pressure conditions within the calibration range to a final set of temperature and pressure conditions within the calibration range. The initial set of temperature and pressure conditions from which the rheological quantity of the drilling fluid is scaled may be the same as any of the first, second or third sets of reference conditions, or the initial set of temperature and pressure conditions may be entirely different. Most typically, the initial set of temperature and pressure conditions from which the rheological quantity is scaled represents a set of conditions where the rheological quantity is most easily measured (i.e., a low temperature and/or low pressure). The final set of temperature and pressure conditions may represent conditions where the rheological quantity is not as easily measured.

It should be noted that the initial set of temperature and pressure conditions or the final set of temperature and pressure conditions may also lie outside of the calibration range defined by the reference conditions. However, in such a situation, one may have a lower degree of confidence that the linear rate of change in apparent viscosity with respect to temperature or pressure or a calibration function defining these values is valid outside the calibration range. When encountering an initial or final set of temperature and pressure conditions outside the defined calibration range, one needs to presume that the linear rate of change or the trend of the calibration function extends unchanged beyond the endpoint(s) of the calibration range. More ideally, the calibration range may be extended using a wider breadth of reference conditions before scaling the rheological quantity from the initial set of temperature and pressure conditions to the final set of temperature and pressure conditions.

The temperature and pressure conditions over which a rheological quantity may be scaled according to the disclosure herein are not believed to be particularly limited. The only apparent limiting factor may be the temperature and pressure conditions under which the apparent viscosity may be effectively measured. For a vibrational viscometer, for example, the calibration range may extend to a temperature up to about 500° F. and a pressure up to about 30,000 psi.

As indicated above, the rates of change in apparent viscosity with respect to temperature and with respect to pressure are based upon measurements at three sets of reference conditions, which are used to define linear rates of change for each parameter (i.e., linear calibration functions in the change in apparent viscosity with respect to temperature and with respect to pressure). If a more accurate determination of the calibration function's shape within the calibration range is desired, the apparent viscosity may be measured at a plurality of reference conditions within the calibration range, each defining a reference temperature and a reference pressure within the calibration range. Plots of the apparent viscosity with respect to temperature and with respect to pressure may then be generated, and regression analyses may then be conducted to fit the plots to an appropriate mathematical function. Any suitable curve fitting protocol may be employed. Taking the derivative of each mathematical function then allows the dU/dT and dU/dP to be determined. Inputting the final temperature and the final pressure into the derivative functions then allows the rate of change at the final temperature and pressure conditions to be determined for applying Equation 1.

In more specific embodiments, the methods may further comprise the following when defining a calibration function: measuring the apparent viscosity of the drilling fluid at a plurality of reference conditions within the calibration range; determining a calibration function for the rate of change in apparent viscosity with respect to temperature and a calibration function for the rate of change in apparent viscosity with respect to pressure over the calibration range; determining from the calibration functions the rate of change in apparent viscosity with respect to temperature and the rate of change in apparent viscosity with respect to pressure at the final set of temperature and pressure conditions; and scaling the rheological quantity measured at the initial set of temperature and pressure conditions within the calibration range to the final set of temperature and pressure conditions within the calibration range, the scaling being calculated based upon the rate of change in apparent viscosity with respect to temperature and the rate of change in apparent viscosity with respect to pressure as determined from the calibration functions at the final set of temperature and pressure conditions, thereby determining the calculated rheological quantity.

In some embodiments, the apparent viscosity itself may be the rheological quantity that is scaled to the final set of temperature and pressure conditions. That is, in some embodiments, the calculated rheological quantity is the apparent viscosity of the drilling fluid at the final set of temperature and pressure conditions. Scaling of the apparent viscosity may be useful, for example, to obtain a qualitative estimate of how the rheological performance of the drilling fluid may change under a particular set of temperature and pressure conditions. Even if the apparent viscosity can be measured at the final set of temperature and pressure conditions, scaling from the initial set of temperature and pressure conditions can avoid having to actually make the measurements.

More advantageously, however, a rheological quantity that is not readily measured under the final set of temperature and pressure conditions may be calculated by utilizing the methods described herein. In more specific embodiments, the calculated rheological quantity is the shear stress of the drilling fluid at the final set of temperature and pressure conditions. As discussed above, determination of the shear stress under extreme temperature and pressure conditions can be slow and cumbersome, issues which are advantageously overcome by practicing the embodiments described herein. By determining the shear stress, an estimation of the equivalent circulating density of the drilling fluid in a wellbore during a drilling operation may be obtained.

In practicing the methods described herein, the apparent viscosity of the drilling fluid under the first, second and third set of reference conditions may be determined in any location. In some embodiments, at least one of the apparent viscosity measurements may be made outside a wellbore, and the remaining apparent viscosity measurements may be made on the drilling fluid while it is in the wellbore and being exposed to the particular reference condition. In other embodiments, the apparent viscosity of the drilling fluid may be measured in a wellbore at the first, second and third set of reference conditions. Measurement of a drilling fluid's apparent viscosity within a wellbore at each of the reference conditions can be particularly desirable in order to most accurately account for the in-process introduction of drill cuttings and other substances within the drilling fluid that may affect its rheological performance. In still other embodiments, the apparent viscosity of the drilling fluid under the first, second and third set of reference conditions may be measured on the drilling fluid outside the wellbore environment.

Any suitable rheology measuring device may be used to determine the apparent viscosity of the drilling fluid under the first, second and third set of reference conditions. Most desirably, the rheology measuring device is one that is readily operated under extreme temperature and pressure conditions, rugged, and configured to provide a rapid output of apparent viscosity data. In some embodiments, the apparent viscosity of the drilling fluid may be measured using a vibrational viscometer, such as those supplied by Sofraser, Inc. These viscometers may be desirable due to their lack of seals and rotating parts. In general, any couette, tube, cone and plate, or parallel plate viscometer may be used in the embodiments of the present disclosure provided that the viscometer can be easily pressurized and heated. Other suitable viscometers for practicing the embodiments described herein may include ultrasonic viscometers, for example.

In more particular embodiments, the apparent viscosity of the drilling fluid may be measured using a vibrational viscometer. The operational details of vibrational viscometers will be well understood by one having ordinary skill in the art and will not be further described herein.

Similarly, the rheological quantity being scaled according to the disclosure herein (e.g., shear stress or shear rate) may be measured at the initial set of temperature and pressure conditions using any suitable rheology measurement device. In some embodiments, the rheological quantity to be scaled may be measured at the initial set of temperature and pressure conditions using a couette-style viscometer, particularly when the rheological quantity is shear rate or shear stress. Suitable couette-style viscometers and processes for their operation will be familiar to one having ordinary skill in the art. Illustrative operational conditions and parameters for a Fann 35 viscometer are described in American Petroleum Institute RP 13D, for example.

Measurement of the rheological quantity of the drilling fluid under the initial set of temperature and pressure conditions may take place in any location where such conditions are present. In some embodiments, the rheological quantity may be measured at the initial set of temperature and pressure conditions outside the wellbore. In these embodiments, a couette-style viscometer, such as a Fann 35 viscometer, may be sufficient. If the initial set of temperature and pressure conditions are outside the working range of a Fann 35 viscometer, a Fann 35 or Fann 77 couette-style viscometer may be used. In other embodiments, the rheological quantity may be measured at the initial set of temperature and pressure conditions within the wellbore. For example, in some embodiments, the shear stress of the drilling fluid at the initial set of temperature and pressure conditions may be measured in the wellbore.

The methods described herein may be further extended to regulate various aspects of a drilling operation. The regulation of the drilling operation may be proactive in some embodiments or reactive in other embodiments. In proactive embodiments, the historical rheology of a particular drilling fluid may be used as a starting point to determine a calculated rheological quantity of the drilling fluid under the specific temperature and pressure conditions present within a given wellbore. The calculated rheological quantity may be used to determine if the drilling fluid is suitable for use in the wellbore or if it needs to be compositionally modified in order to become suitable for use. In reactive embodiments, measurement of the drilling fluid's apparent viscosity in the wellbore and determination of the calculated rheological quantity may help direct an adjustment to the drilling operation while it is ongoing. In some embodiments, adjustment of the drilling operation may comprise modifying the composition of the drilling fluid on-the-fly. In some or other embodiments, adjustment of the drilling operation may comprise modifying one or more drilling parameters.

The equivalent circulating density (ECD) of a drilling fluid downhole may be determined based upon the drilling fluid's shear stress. By applying the disclosure herein, the calculated shear stress or another calculated rheological quantity may be used to obtain an estimate of the drilling fluid's ECD at the final set of temperature and pressure conditions. If the estimated ECD is outside a desired range and the drilling fluid does not have the correct properties to adequately perform the drilling operation, subsequently introduced drilling fluid may be modified to address this deficiency or a parameter of the drilling operation may be adjusted. Parameters of the drilling operation that may be modified include, for example, flow rate and rate of penetration. In proactive embodiments, the ECD of the drilling fluid may be estimated prior to its use in drilling a wellbore.

In some embodiments, methods described herein may comprise determining an equivalent circulating density of the drilling fluid at the final set of temperature and pressure conditions based upon the calculated rheological quantity, particularly a calculated value for shear stress. The final set of temperature and pressure conditions may vary considerably depending on the particular position within the wellbore at which the measurement is being made. Determining an ECD may comprise inputting the calculated shear stress or a related rheological quantity into an appropriate formula for calculating the ECD. Suitable formulas for calculating an ECD will be familiar to one having ordinary skill in the art. In further embodiments, the drilling operation may be regulated in response to the equivalent circulating density determined from the calculated rheological quantity.

In some embodiments, the calculated rheological quantity may be determined in real-time or near real-time. Real-time or near real-time output of the calculated rheological quantity may allow reactive adjustment of the drilling operation to take place.

Moreover, in some embodiments, regulating the drilling operation may take place automatically under computer control in response to the calculated rheological quantity or the quantity derived therefrom. Regulation of the drilling operation may involve applying appropriate algorithms, neural networks or other artificial intelligence means to determine an appropriate course of action for modifying the drilling operation. For example, a computer may utilize an algorithm-based approach to determine how an ECD will change in response to a change in a rheological quantity. The computer may then further apply the algorithm to adjust any parameter of the drilling operation or the composition of the drilling fluid in order to produce a desired outcome.

The exemplary drilling fluids and processes disclosed herein may directly or indirectly affect one or more components or pieces of equipment associated with the preparation, delivery, recapture, recycling, reuse, and/or disposal of the disclosed drilling fluids. For example, and with reference to FIG. 1, the disclosed drilling fluids may directly or indirectly affect one or more components or pieces of equipment associated with an exemplary wellbore drilling assembly 100, according to one or more embodiments. It should be noted that while FIG. 1 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 100 may include a drilling platform 102 that supports a derrick 104 having a traveling block 106 for raising and lowering a drill string 108. The drill string 108 may include, but is not limited to, drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 from the well surface. As the bit 114 rotates, it creates a borehole 116 that penetrates various subterranean formations 118.

A pump 120 (e.g., a mud pump) circulates drilling fluid 122 through a feed pipe 124 and to the kelly 110, which conveys the drilling fluid 122 downhole through the interior of the drill string 108 and through one or more orifices in the drill bit 114. The drilling fluid 122 is then circulated back to the surface via an annulus 126 defined between the drill string 108 and the walls of the borehole 116. At the surface, the recirculated or spent drilling fluid 122 exits the annulus 126 and may be conveyed to one or more fluid processing unit(s) 128 via an interconnecting flow line 130. After passing through the fluid processing unit(s) 128, a "cleaned" drilling fluid 122 is deposited into a nearby retention pit 132 (i.e., a mud pit). While illustrated as being arranged at the outlet of the wellbore 116 via the annulus 126, those skilled in the art will readily appreciate that the fluid processing unit(s) 128 may be arranged at any other location in the drilling assembly 100 to facilitate its proper function, without departing from the scope of the disclosure.

One or more of the disclosed drilling fluids may be added to the drilling fluid 122 via a mixing hopper 134 communicably coupled to or otherwise in fluid communication with the retention pit 132. The mixing hopper 134 may include, but is not limited to, mixers and related mixing equipment known to those skilled in the art. In other embodiments, however, the disclosed drilling fluids may be added to the drilling fluid 122 at any other location in the drilling assembly 100. In at least one embodiment, for example, there could be more than one retention pit 132, such as multiple retention pits 132 in series. Moreover, the retention pit 132 may be representative of one or more fluid storage facilities and/or units where the disclosed drilling fluids may be stored, reconditioned, and/or regulated until added to the drilling fluid 122.

As mentioned above, the disclosed drilling fluids may directly or indirectly affect the components and equipment of the drilling assembly 100. For example, the disclosed drilling fluids may directly or indirectly affect the fluid processing unit(s) 128 which may include, but is not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The fluid processing unit(s) 128 may further include one or more sensors, gauges, pumps, compressors, and the like used to store, monitor, regulate, and/or recondition the exemplary drilling fluids.

The disclosed drilling fluids may directly or indirectly affect the pump 120, which representatively includes any conduits, pipelines, trucks, tubulars, and/or pipes used to fluidically convey the drilling fluids downhole, any pumps, compressors, or motors (e.g., topside or downhole) used to drive the drilling fluids into motion, any valves or related joints used to regulate the pressure or flow rate of the drilling fluids, and any sensors (i.e., pressure, temperature, flow rate, etc.), gauges, and/or combinations thereof, and the like. The disclosed drilling fluids may also directly or indirectly affect the mixing hopper 134 and the retention pit 132 and their assorted variations.

The disclosed drilling fluids may also directly or indirectly affect the various downhole equipment and tools that may come into contact with the drilling fluids such as, but not limited to, the drill string 108, any floats, drill collars, mud motors, downhole motors and/or pumps associated with the drill string 108, and any MWD/LWD tools and related telemetry equipment, sensors or distributed sensors associated with the drill string 108. The disclosed drilling fluids may also directly or indirectly affect any downhole heat exchangers, valves and corresponding actuation devices, tool seals, packers and other wellbore isolation devices or components, and the like associated with the wellbore 116. The disclosed drilling fluids may also directly or indirectly affect the drill bit 114, which may include, but is not limited to, roller cone bits, PDC bits, natural diamond bits, any hole openers, reamers, coring bits, etc.

While not specifically illustrated herein, the disclosed drilling fluids may also directly or indirectly affect any transport or delivery equipment used to convey the drilling fluids to the drilling assembly 100 such as, for example, any transport vessels, conduits, pipelines, trucks, tubulars, and/ or pipes used to fluidically move the drilling fluids from one location to another, any pumps, compressors, or motors used to drive the drilling fluids into motion, any valves or related joints used to regulate the pressure or flow rate of the drilling fluids, and any sensors (i.e., pressure and temperature), gauges, and/or combinations thereof, and the like.

Embodiments disclosed herein include:

A. Methods for calculating a rheological quantity. The methods comprise: measuring an apparent viscosity of a drilling fluid at a first set of reference conditions comprising a first reference temperature and a first reference pressure, at a second set of reference conditions comprising a second reference temperature and a second reference pressure, and at a third set of reference conditions comprising a third reference temperature and a third reference pressure; wherein at least two of the reference temperatures are substantially equal to one another and at least two of the reference pressures are substantially equal to one another, the reference temperatures and the reference pressures defining a calibration range; determining a rate of change in apparent viscosity with respect to temperature between two of the sets of reference conditions in which the reference pressures are substantially equal; determining a rate of change in apparent viscosity with respect to pressure between two of the sets of reference conditions in which the reference temperatures are substantially equal; and scaling a rheological quantity measured at an initial set of temperature and pressure conditions within the calibration range to a final set of temperature and pressure conditions within the calibration range, the scaling being calculated based upon the rate of change in apparent viscosity with respect to temperature and the rate of change in apparent viscosity with respect to pressure, thereby determining a calculated rheological quantity.

B. Methods for regulating a drilling operation. The methods comprise: introducing a drilling fluid into a wellbore during a drilling operation; measuring an apparent viscosity of the drilling fluid at a first set of reference conditions comprising a first reference temperature and a first reference pressure, at a second set of reference conditions comprising a second reference temperature and a second reference pressure, and at a third set of reference conditions comprising a third reference temperature and a third reference pressure; wherein at least two of the reference temperatures are substantially equal to one another and at least two of the reference pressures are substantially equal to one another, the reference temperatures and the reference pressures defining a calibration range; determining a rate of change in apparent viscosity with respect to temperature between two of the sets of reference conditions in which the reference pressures are substantially equal; determining a rate of change in apparent viscosity with respect to pressure between two of the sets of reference conditions in which the reference temperatures are substantially equal; scaling a rheological quantity measured at an initial set of temperature and pressure conditions within the calibration range to a final set of temperature and pressure conditions within the calibration range, the scaling being calculated based upon the rate of change in apparent viscosity with respect to temperature and the rate of change in apparent viscosity with respect to pressure, thereby determining a calculated rheological quantity; and regulating the drilling operation in response to the calculated rheological quantity of the drilling fluid or a quantity derived therefrom.

Each of embodiments A and B may have one or more of the following additional elements in any combination:

Element 1: wherein scaling the rheological quantity comprises solving the equation:

$$Q_F = Q_I + Q_I[(dU/dT)(T_F - T_I) + (dU/dP)(P_F - P_I)];$$

wherein:
$Q_F$ is the calculated rheological quantity at the final set of temperature and pressure conditions;
$Q_I$ is a measured value of the rheological quantity at the initial set of temperature and pressure conditions;
$dU/dT$ is the rate of change in apparent viscosity with respect to temperature;
$dU/dP$ is the rate of change in apparent viscosity with respect to pressure;
$T_F$ is the temperature at the final set of temperature and pressure conditions;
$T_I$ is the temperature at the initial set of temperature and pressure conditions;
$P_F$ is the pressure at the final set of temperature and pressure conditions; and
$P_I$ is the pressure at the initial set of temperature and pressure conditions.

Element 2: wherein the method further comprises determining an equivalent circulating density of the drilling fluid at the final set of temperature and pressure conditions based upon the calculated rheological quantity.

Element 3: wherein the apparent viscosity of the drilling fluid is measured in a wellbore at the first, second and third set of reference conditions.

Element 4: wherein the apparent viscosity of the drilling fluid is measured using a vibrational viscometer.

Element 5: wherein the calculated rheological quantity is the apparent viscosity of the drilling fluid at the final set of temperature and pressure conditions.

Element 6: wherein the calculated rheological quantity is shear stress of the drilling fluid at the final set of temperature and pressure conditions.

Element 7: wherein the shear stress of the drilling fluid at the initial set of temperature and pressure conditions is measured using a couette-style viscometer.

Element 8: wherein the method further comprises: measuring the apparent viscosity of the drilling fluid at a plurality of reference conditions within the calibration range; determining a calibration function for the rate of change in apparent viscosity with respect to temperature and a calibration function for the rate of change in apparent viscosity with respect to pressure over the calibration range; determining from the calibration functions the rate of change in apparent viscosity with respect to temperature and the rate of change in apparent viscosity with respect to pressure at the final set of temperature and pressure conditions; and scaling the rheological quantity measured at the initial set of temperature and pressure conditions within the calibration range to the final set of temperature and pressure conditions within the calibration range, the scaling being calculated based upon the rate of change in apparent viscosity with respect to temperature and the rate of change in apparent viscosity with respect to pressure as determined from the calibration functions at the final set of temperature and pressure conditions, thereby determining the calculated rheological quantity.

The apparent viscosity data from Reference Condition 1 was then scaled to three additional sets of temperature and pressure conditions (Entries 4-6), as also specified in Table 1, using Formula 1 above.

TABLE 1

| Entry | Measured Values | | | Calculated Values | | | | |
|---|---|---|---|---|---|---|---|---|
| | Reference Condition 1 | Reference Condition 2 | Reference Condition 3 | Calculated dU/dT | Calculated dU/dP | 4 | 5 | 6 |
| Temperature (° F) | 120 | 350 | 350 | | | 40 | 225 | 350 |
| Pressure (psi) | 100 | 100 | 10000 | | | 5000 | 10000 | 15000 |
| Apparent Viscosity (cP) | 50 | 25 | 65 | $-0.0021739$ | $3.03 \times 10^{-5}$ | 66.1 | 53.6 | 47.6 |

Element 9: wherein the drilling operation is regulated in response to the equivalent circulating density determined from the calculated rheological quantity.

Element 10: wherein regulating the drilling operation takes place automatically under computer control in response to the calculated rheological quantity or the quantity derived therefrom.

By way of non-limiting example, exemplary combinations applicable to A and B include:

The method of A in combination with elements 1 and 2.
The method of A in combination with elements 1 and 4.
The method of A in combination with elements 1, 3 and 4.
The method of A in combination with elements 2 and 4.
The method of A in combination with elements 4 and 5.
The method of A in combination with elements 4 and 6.
The method of A in combination with elements 4, 6 and 7.
The method of B in combination with elements 1 and 2.
The method of B in combination with elements 1 and 4.
The method of B in combination with elements 2, 4 and 9.
The method of B in combination with elements 2 and 4.
The method of B in combination with elements 4 and 5.
The method of B in combination with elements 4 and 6.
The method of B in combination with elements 4, 6 and 7.

To facilitate a better understanding of the embodiments of the present disclosure, the following examples of preferred or representative embodiments are given. In no way should the following examples be read to limit, or to define, the scope of the disclosure.

EXAMPLES

Example 1

The apparent viscosity of a drilling fluid was measured using a vibrational viscometer at three sets of reference temperature and pressure conditions, as specified in Table 1. Comparing Reference Condition 1 and Reference Condition 2, dU/dT was determined, and comparing Reference Condition 2 and Reference Condition 3, dU/dP was determined.

Figure 2:
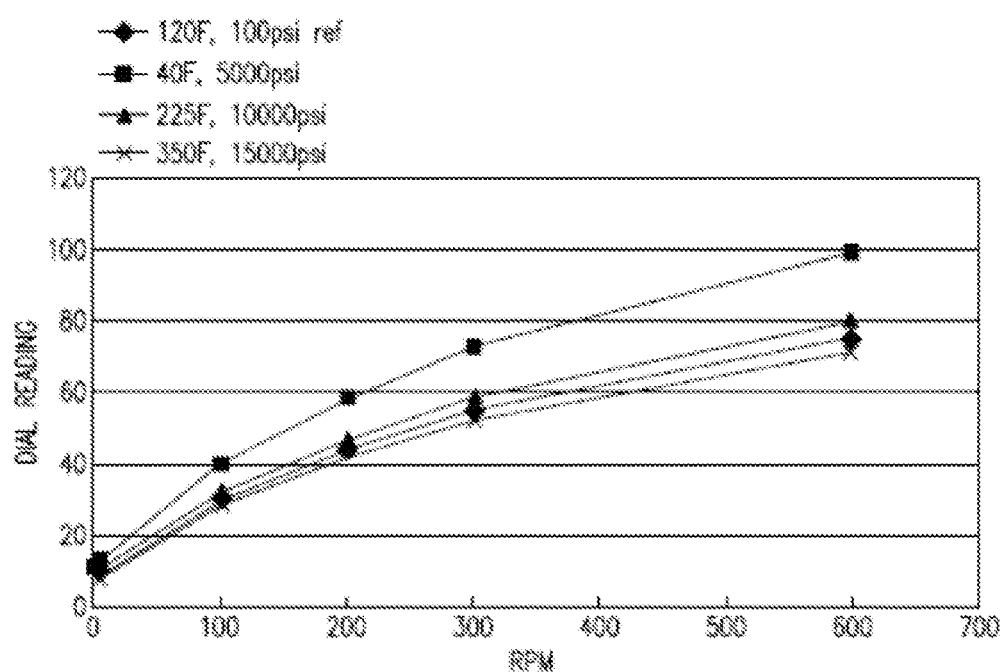
FIG. 2 shows a plot demonstrating how the Fann 35 dial reading varies for a drilling fluid over a range of rotation rates at various temperatures and pressures.

In a similar manner, the drilling fluid was assayed using a Fann 35 viscometer at various shear rates at a single set of temperature and pressure conditions. The testing data is summarized in Table 2. The single set of temperature and pressure conditions at which the Fann 35 measurements were made correspond to those of Reference Condition 1 (Entry 1' in Table 2). The dial readings were then scaled to the temperature and pressure conditions of Reference Conditions 2 and 3 (Entries 2' and 3' in Table 2) and those of Entries 4-6 from Table 1 (Entries 4'-6' in Table 2). FIG. 2 shows a plot demonstrating how the Fann 35 dial reading varies for a drilling fluid over a range of rotation rates at various temperatures and pressures.

TABLE 2

| Entry | Measured Value | Calculated Values | | | | |
|---|---|---|---|---|---|---|
| | 1' | 2' | 3' | 4' | 5' | 6' |
| Temperature (° F.) | 120 | 350 | 350 | 40 | 225 | 350 |
| Pressure (psi) | 100 | 100 | 10000 | 5000 | 10000 | 15000 |
| Fann 35 Dial Reading | | | | | | |
| 600 | 75 | 37.5 | 60.0 | 99.2 | 80.4 | 71.4 |
| 300 | 55 | 27.5 | 44.0 | 72.7 | 58.9 | 52.3 |
| 200 | 44 | 22.0 | 35.2 | 58.2 | 47.2 | 41.9 |
| 100 | 30 | 15.0 | 24.0 | 39.7 | 32.2 | 28.5 |
| 6 | 10 | 5.0 | 8.0 | 13.2 | 10.7 | 9.5 |
| 3 | 8 | 4.0 | 6.4 | 10.6 | 8.6 | 7.6 |

Unless otherwise indicated, all numbers expressing quantities of ingredients, properties such as molecular weight, reaction conditions, temperature, rheological conditions and so forth used in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
   measuring an apparent viscosity of a drilling fluid at a first set of reference conditions comprising a first reference temperature and a first reference pressure, at a second set of reference conditions comprising a second reference temperature and a second reference pressure, and at a third set of reference conditions comprising a third reference temperature and a third reference pressure;
   wherein at least two of the reference temperatures are substantially equal to one another and at least two of the reference pressures are substantially equal to one another, the reference temperatures and the reference pressures defining a calibration range;
   determining a rate of change in apparent viscosity with respect to temperature between two of the sets of reference conditions in which the reference pressures are substantially equal;
   determining a rate of change in apparent viscosity with respect to pressure between two of the sets of reference conditions in which the reference temperatures are substantially equal; and
   scaling a rheological quantity measured at an initial set of temperature and pressure conditions within the calibration range to a final set of temperature and pressure conditions within the calibration range, the scaling being calculated based upon the rate of change in apparent viscosity with respect to temperature and the rate of change in apparent viscosity with respect to pressure, thereby determining a calculated rheological quantity.

2. The method of claim 1, wherein scaling the rheological quantity comprises solving the equation:

$$Q_F = Q_I + Q_I[(dU/dT)(T_F - T_I) + (dU/dP)(P_F - P_I)];$$

wherein:
$Q_F$ is the calculated rheological quantity at the final set of temperature and pressure conditions;
$Q_I$ is a measured value of the rheological quantity at the initial set of temperature and pressure conditions;
$dU/dT$ is the rate of change in apparent viscosity with respect to temperature;
$dU/dP$ is the rate of change in apparent viscosity with respect to pressure;
$T_F$ is the temperature at the final set of temperature and pressure conditions;
$T_I$ is the temperature at the initial set of temperature and pressure conditions;
$P_F$ is the pressure at the final set of temperature and pressure conditions; and,
$P_I$ is the pressure at the initial set of temperature and pressure conditions.

3. The method of claim 1, further comprising:
   determining an equivalent circulating density of the drilling fluid at the final set of temperature and pressure conditions based upon the calculated rheological quantity.

4. The method of claim 1, wherein the apparent viscosity of the drilling fluid is measured in a wellbore at the first, second and third set of reference conditions.

5. The method of claim 1, wherein the apparent viscosity of the drilling fluid is measured using a vibrational viscometer.

6. The method of claim 1, wherein the calculated rheological quantity is the apparent viscosity of the drilling fluid at the final set of temperature and pressure conditions.

7. The method of claim 1, wherein the calculated rheological quantity is shear stress of the drilling fluid at the final set of temperature and pressure conditions.

8. The method of claim 7, wherein the shear stress of the drilling fluid at the initial set of temperature and pressure conditions is measured using a couette-style viscometer.

9. The method of claim 8, wherein the apparent viscosity of the drilling fluid is measured using a vibrational viscometer.

10. The method of claim 8, wherein the apparent viscosity of the drilling fluid is measured in a wellbore at the first, second and third set of reference conditions.

11. The method of claim 1, further comprising:
    measuring the apparent viscosity of the drilling fluid at a plurality of reference conditions within the calibration range;
    determining a calibration function for the rate of change in apparent viscosity with respect to temperature and a calibration function for the rate of change in apparent viscosity with respect to pressure over the calibration range;
    determining from the calibration functions the rate of change in apparent viscosity with respect to temperature and the rate of change in apparent viscosity with respect to pressure at the final set of temperature and pressure conditions; and
    scaling the rheological quantity measured at the initial set of temperature and pressure conditions within the calibration range to the final set of temperature and pressure conditions within the calibration range, the scaling being calculated based upon the rate of change in apparent viscosity with respect to temperature and the rate of change in apparent viscosity with respect to pressure as determined from the calibration functions at the final set of temperature and pressure conditions, thereby determining the calculated rheological quantity.

12. A method comprising:
introducing a drilling fluid into a wellbore during a drilling operation;
measuring an apparent viscosity of the drilling fluid at a first set of reference conditions comprising a first reference temperature and a first reference pressure, at a second set of reference conditions comprising a second reference temperature and a second reference pressure, and at a third set of reference conditions comprising a third reference temperature and a third reference pressure;
wherein at least two of the reference temperatures are substantially equal to one another and at least two of the reference pressures are substantially equal to one another, the reference temperatures and the reference pressures defining a calibration range;
determining a rate of change in apparent viscosity with respect to temperature between two of the sets of reference conditions in which the reference pressures are substantially equal;
determining a rate of change in apparent viscosity with respect to pressure between two of the sets of reference conditions in which the reference temperatures are substantially equal;
scaling a rheological quantity measured at an initial set of temperature and pressure conditions within the calibration range to a final set of temperature and pressure conditions within the calibration range, the scaling being calculated based upon the rate of change in apparent viscosity with respect to temperature and the rate of change in apparent viscosity with respect to pressure, thereby determining a calculated rheological quantity; and
regulating the drilling operation in response to the calculated rheological quantity of the drilling fluid or a quantity derived therefrom.

13. The method of claim 12, wherein scaling the rheological quantity comprises solving the equation:

$$Q_F = Q_I + Q_I[(dU/dT)(T_F - T_I) + (dU/dP)(P_F - P_I)];$$

wherein:
$Q_F$ is the calculated rheological quantity at the final set of temperature and pressure conditions;
$Q_I$ is a measured value of the rheological quantity at the initial set of temperature and pressure conditions;
$dU/dT$ is the rate of change in apparent viscosity with respect to temperature;
$dU/dP$ is the rate of change in apparent viscosity with respect to pressure;
$T_F$ is the temperature at the final set of temperature and pressure conditions;
$T_I$ is the temperature at the initial set of temperature and pressure conditions;
$P_F$ is the pressure at the final set of temperature and pressure conditions; and
$P_I$ is the pressure at the initial set of temperature and pressure conditions.

14. The method of claim 12, wherein the apparent viscosity of the drilling fluid is measured using a vibrational viscometer.

15. The method of claim 12, further comprising:
determining an equivalent circulating density of the drilling fluid in the wellbore at the final set of temperature and pressure conditions based upon the calculated rheological quantity.

16. The method of claim 15, wherein the drilling operation is regulated in response to the equivalent circulating density determined from the calculated rheological quantity.

17. The method of claim 12, wherein the calculated rheological quantity is the apparent viscosity of the drilling fluid at the final set of temperature and pressure conditions.

18. The method of claim 12, wherein the calculated rheological quantity is shear stress of the drilling fluid at the final set of temperature and pressure conditions.

19. The method of claim 18, wherein the shear stress of the drilling fluid at the initial set of temperature and pressure conditions is measured using a couette-style viscometer.

20. The method of claim 19, wherein the apparent viscosity of the drilling fluid is measured using a vibrational viscometer.

21. The method of claim 12, wherein regulating the drilling operation takes place automatically under computer control in response to the calculated rheological quantity or the quantity derived therefrom.

22. The method of claim 12, further comprising:
measuring the apparent viscosity of the drilling fluid at a plurality of reference conditions within the calibration range;
determining a calibration function for the rate of change in apparent viscosity with respect to temperature and a calibration function for the rate of change in apparent viscosity with respect to pressure over the calibration range;
determining from the calibration functions the rate of change in apparent viscosity with respect to temperature and the rate of change in apparent viscosity with respect to pressure at the final set of temperature and pressure conditions; and
scaling the rheological quantity measured at the initial set of temperature and pressure conditions within the calibration range to the final set of temperature and pressure conditions within the calibration range, the scaling being calculated based upon the rate of change in apparent viscosity with respect to temperature and the rate of change in apparent viscosity with respect to pressure as determined from the calibration functions at the final set of temperature and pressure conditions, thereby determining the calculated rheological quantity.

* * * * *